United States Patent [19]  [11] 3,970,075
Sindelar et al.  [45] July 20, 1976

[54] SURGICAL RETRACTOR ANCHOR APPARATUS

[76] Inventors: Frank J. Sindelar, 8 Kimball Road; Howard J. Greenfield, 32 Yates Blvd., both of Poughkeepsie, N.Y. 12601

[22] Filed: Sept. 30, 1974

[21] Appl. No.: 510,218

[52] U.S. Cl. .................................................. 128/20
[51] Int. Cl.² ........................................... A61B 17/02
[58] Field of Search .................. 128/20, 303 R, 341, 128/303 A, 346

[56] References Cited
UNITED STATES PATENTS

| | | | |
|---|---|---|---|
| 649,854 | 5/1900 | Lundborg | 128/20 |
| 1,747,799 | 2/1930 | Straus | 128/20 |
| 2,586,488 | 2/1952 | Smith | 128/20 |
| 2,612,891 | 10/1952 | Smith | 128/20 |
| 2,701,562 | 2/1955 | Michael et al. | 128/20 |
| 3,572,326 | 3/1971 | Jensen | 128/20 |
| 3,665,926 | 5/1972 | Flores | 128/346 |
| 3,823,709 | 7/1974 | McGuire | 128/20 |

Primary Examiner—Robert W. Michell
Assistant Examiner—Henry S. Layton
Attorney, Agent, or Firm—Joseph L. Spiegel

[57] ABSTRACT

Apparatus for fixing retractors in an adjustable, predetermined position relative to a patient on an operating table. The apparatus comprises an anchor frame including a base member having at least one extension member projecting substantially perpendicular to the base member. A plurality of spaced apart, inwardly projecting anchor rings are serially arranged along the anchor frame, and a support frame, including upstanding post members is connected for supporting the base member of the anchor frame. Legs are adjustably clamped to the post members, the legs in turn being adjustably connected to the operating table. The adjustable connection of the legs to the post members is such as to clamp the post members and thus the anchor frame at a preselected and predetermined height relative to a patient on the operating table. Resilient bands are connected to preselected ones of the anchor rings, which bands include retractors thereon for separating an incision under a predetermined tension and with a predetermined opening desired by the surgeon.

The purpose of this abstract is to enable the Public and the Patent Office to determine the subject matter of the technical disclosure of the application. This abstract is neither intended to define the invention of the application nor is it intended to be limiting as to the scope thereof.

10 Claims, 5 Drawing Figures

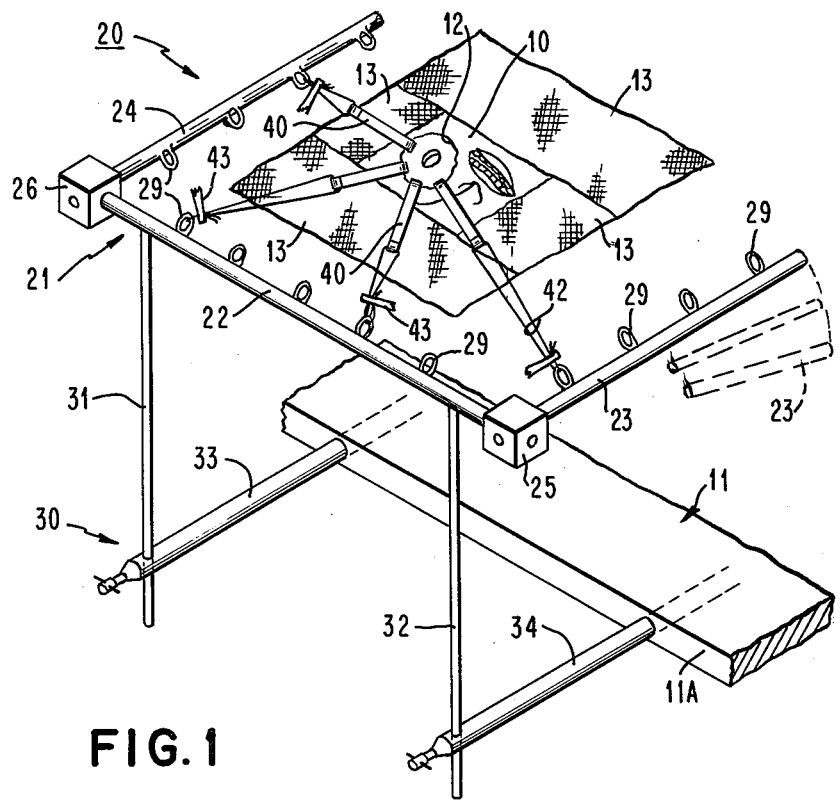
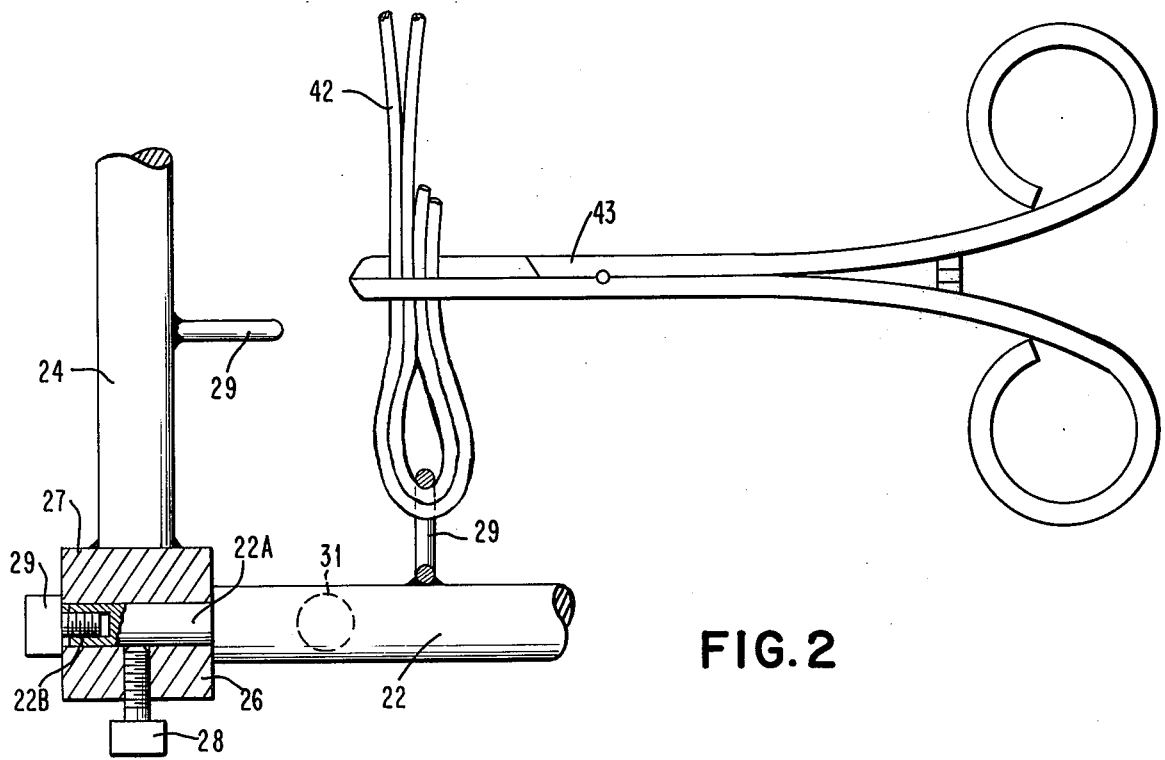
FIG. 1
FIG. 2

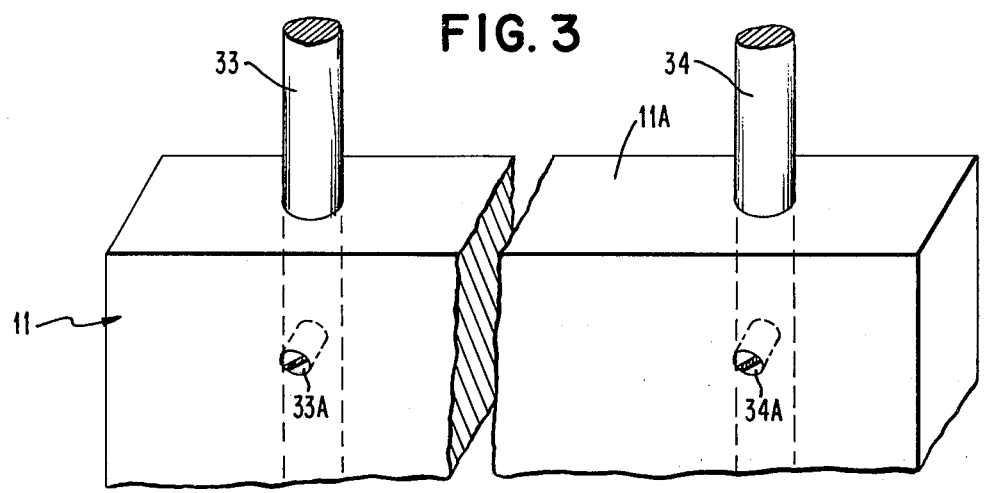
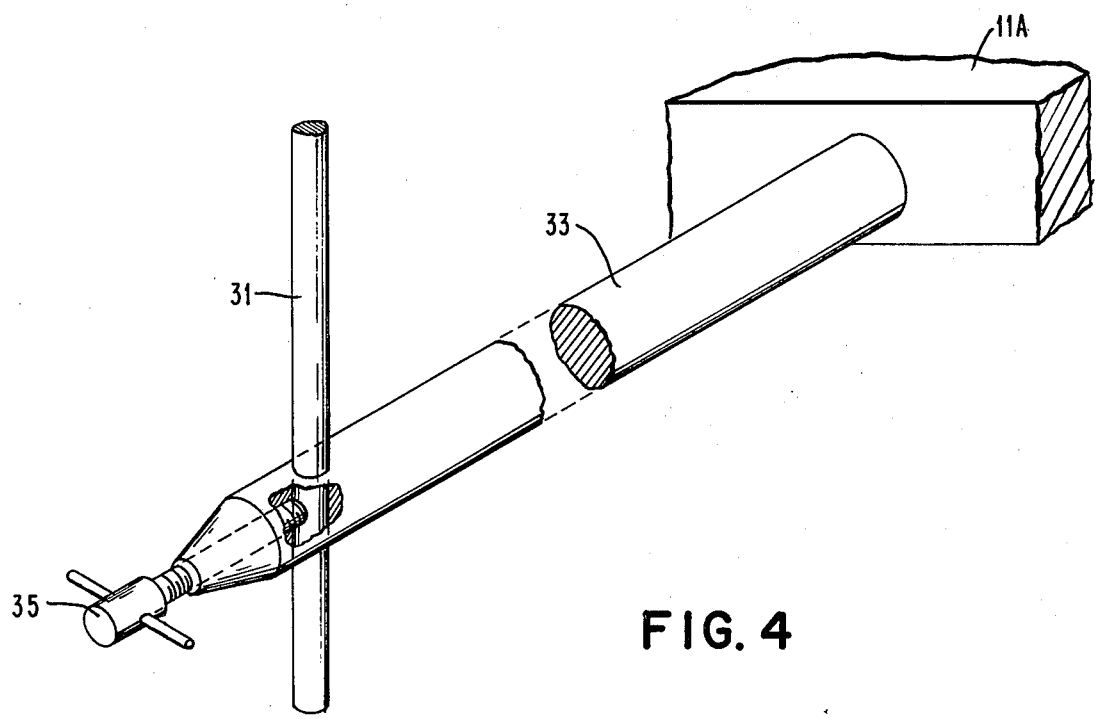
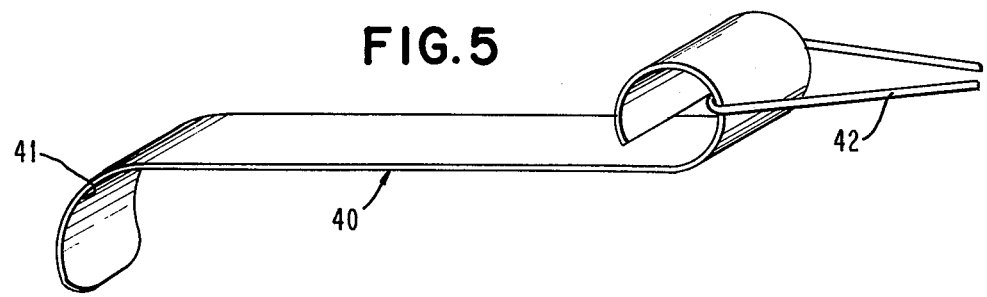

SURGICAL RETRACTOR ANCHOR APPARATUS

SUMMARY OF THE INVENTION AND STATEMENT OF THE PRIOR ART

The present invention relates to surgical apparatus or instruments and more particularly to a surgical retractor anchor apparatus for positioning and tensioning surgical retractors on a patient on an operating table.

In conventional surgical procedures the physician normally makes use of devices called retractors to hold the incision open. The shape or design of the retractor utilized to maintain the incision in an open condition, depends upon the surgeon's particular field of expertise, for example in the field of rhinology the retractors are generally S-shaped having hooks at opposite ends, one end of the hook entering into the flesh of the patient while the opposite end serves as a holder for an elastic band.

Conventionally, one end of the elastic band is attached to one hooked end of the retractor and the opposite end may be tied or otherwise fastened to a screw or the like on the operating table. Such attachment of the band is of course cumbersome and in many instances does not provide the surgeon with a preferred angle of pull on the incision.

There are numerous instances in the prior art where special instruments have been provided for attachment to the patient for hooking the elastic bands and holding the retractors in a specific position to hold the wound open. Such design, of course, is difficult if not impossible to employ in, for example, the field of rhinology where the surgical procedure involves the head or face of the patient. Such instruments which utilizes the patient's body as an anchor is illustrated in U.S. Pat. No. 2,701,562. There are numerous other examples of special holders or retainers for surgical retractors all of which have limitations as to their flexibility of position with regard to the patient, or with regard to their ability to be used either singly or at any preselected position or in multiples to permit retraction from obtuse angles to maintain the incision in an open and operative position.

In view of the above, it is a principal object of the present invention to provide novel apparatus for fixing retractors in an adjustably predetermined position relative to an operating table, and mounted thereon to insure the necessary rigidity of and anchoring for surgical retractors.

Another object of the present invention is to provide a surgical retractor anchor apparatus which is fully adjustable in both the horizontal and vertical planes so as to assure the correct positioning and correct angle of pull of and on the retractor.

Still another object of the present invention is to provide a surgical retractor anchor which while being adjustably connected to an operating table, is easily detachable as well as being adjustable to inhibit restriction of the surgeon's movement around the operating table.

Yet another object of the present invention is to provide a novel surgical retractor anchor in which the tension on the elastic or resilient bands holding the retractors may be selectively adjustable to minimize tissue trauma to the patient.

Yet another object of the present invention is to provide on the novel surgical retractor frame, a plurality of positions for connection of the bands holding the retractors so as to permit easy and rapid selection by the surgeon of a connection of the band to the frame thereby selecting the proper angle of pull of the retractor without resorting to a mechanical adjustment.

Other objects and a more complete understanding of the invention may be had by referring to the following specification and claims taken in conjunction with accompanying drawing in which:

FIG. 1 is a fragmentary perspective view of apparatus constructed in accordance with the present invention;

FIG. 2 is an enlarged fragmentary section and plan view of a portion of the apparatus illustrated in FIG. 1;

FIG. 3 is an enlarged fragmentary sectional perspective view of a portion of the apparatus illustrated in FIG. 1;

FIG. 4 is a fragmentary enlarged perspective sectional view of another portion of the apparatus illustrated in FIG. 1; and FIG. 5 is an enlarged fragmentary perspective view of a typical retractor used for maintaining an incision in an open position.

Referring now to the drawing, and especially FIG. 1 thereof, a portion of the head 10 of a patient (remainder not shown) upon which a sinus or sinusital operation is being performed is illustrated as being on an operating table 11, portions of which have been removed for clarity of the apparatus of the present invention. The facial area surrounding an incision 12 is, as is conventional, covered by surgical napkins, cloths or gauze 13.

In accordance with the invention, apparatus 20 is provided for fixing retractors 40 in an adjustably predetermined position relative to the operating table and thus the incision 12 in the facial area 10 of the patient. To this end, the apparatus includes an anchor frame 21 including a first rigid or base member 22 and at least one, in the present instance pair of extension members 23 and 24 projecting substantially perpendicular to the base member 22 and connected thereto as by adjustable clamping means 25 and 26. Mounted on the anchor frame 21, and more specifically on the base member 22 and extension members 23 and 24 are a plurality of spaced apart, inwardly projecting anchor rings 29 which are serially arranged therealong.

In order to provide a rigid but adjustable support for the anchor frame, while permitting the frame to be movable with respect to the patient, the anchor frame 21 is mounted on a support frame 30 which is adjustably connected to a part or portion of 11A of the operating table 11. To this end, the support frame 30 comprises a pair of upstanding post members 31 and 32, each connected to and supporting the base member 22 of the anchor frame 21. The post members are connected to the portion 11A of the operating table as by leg means 33 and 34 which, as best illustrated in FIG. 3, are adjustably connected to the operating table as by set screws 33A and 34A which permit the support frame to be moved towards and away from the operating table in any desired predetermined position, and thus permit location of the anchor frame 21 at any desired position in a plane closer to or remote from the patient.

In order to permit the support frame and thus the anchor frame 21 to be positioned vertically relative to the patient on the operating table, and as best illustrated in FIG. 4, each of the leg means 33 and 34 is provided with an aperture so that the post members may be moved vertically within the apertures.

In order to clamp the anchor frame 21 at its desired height above the patient, locking means 35 is provided for each of the post leg combinations, in the illustrated instance the locking means 35 comprising a bolt or the like, threaded into the legs 33 and 34 and adapted to engage and clamp the posts 31 relative to its associated leg. In this manner due to the set screws 33A and 34A the anchor frame may be positioned in any desired horizontal position relative to the patient and may be positioned in any desired vertical position because of the adjustability of the post members 31 and 32 relative to the legs 33 and 34.

After the anchor frame is positioned both vertically and horizontally in its desired and predetermined position, the surgeon, after the incision has been made applies the retractors 40 to the incision. To this end and as heretofore set forth, the retractors may take any of several forms, one form being illustrated in FIG. 5 wherein a generally S-shaped retractor 40 is illustrated, the retractor including an incision or working end 41 which is applied to the wall of the incision, and a loop or terminal end 41A through which a resilient band or the like 42 may be placed. The surgeon may loop the resilient band 42 through any one of the anchor rings 29, which ring would be selected upon the basis of the desired angle for maintaining the incision open for best viewing during the operative procedure. As shown, one end of the resilient bands 42 may be passed through an anchor ring and then the band held in place as by a simple surgical hemostat 43. In this manner, the proper tension may be placed on the retractor by the surgeon either prior to applying the retractor or subsequent thereto, and depends totally, therefore, upon the desired force necessary to be applied to maintain the walls of the incision in an open condition for proper viewing by the surgeon. Additionally, inasmuch as the rings 29 are arranged in a serial spaced-apart fashion and project inwardly along the anchor frame, the surgeon has the choice of selection of one or more of the anchor rings for proper angle of pull of the retractor or retractors relative to the incision.

In certain instances it may be desirable to vary the angle of pull of one or more retractors relative to other retractors gripping the walls of the incision. To this end and in accordance with a preferred embodiment, at least one of the extensions 23 and 24, in the illustrated instance both of the extensions, are connected to the base member as by adjustable clamping means 25 and 26 respectively, in order to permit rotation of the extension in an arcuate manner about the base member 22. To this end, and referring now to FIG. 2, the base member 22 includes a shaft 22A which projects from opposite terminal ends of the base member 22, each shaft projecting into a sleeve 27 which is connected to an extension which permits rotatable or arcuate movement of the extension about the shaft 22A. In order to clamp the extension in any desired arcuate position relative to the base member 22, a simple set screw 28 or the like passes through the sleeve at right angles to the shaft 22A and serves to clamp the sleeve to the shaft. As an additional locking device, it may be desired to thread the terminal end of the shaft 22A as at 22B and insert a second locking screw 29 therein which, while permitting rotation of its associated extension, in the instance of FIG. 2 extension 24, prevents the extension from moving away from or separating from the base member 22. Additionally, in instances where only a single extension is desired, or where the base member may be utilized as the sole anchor for the retractors, one or both of the extensions may be removed merely by loosening the screw 29 and, of course the locking screw 28 and removal of the extension is thus facilitated.

Thus the apparatus of the present invention provides a simple and yet fully adjustable anchor for fixing retractors in an adjustably predetermined position relative to an operating table. Additionally, by the use of elastic bands, the serial arrangement of the anchor rings, and the capability of arcuate adjustment of the extensions, any desired angle and tension of pull may be selected on the retractors for separating and holding apart the walls of an incision.

Although the invention has been described with a certain degree of particularity, it is understood that the present disclosure has been made only by way of example and that numerous changes and omissions in the details of construction, the combination and arrangement of parts, and the method of operation may be made without departing from the spirit and scope of the invention as hereinafter claimed.

What is claimed is:

1. Apparatus for fixing retractors in an adjustably predetermined position relative to an operating table, said apparatus comprising:
    an anchor frame including a base member having at least one extension member projecting substantially perpendicular to said base member, a plurality of spaced apart, inwardly projecting anchor rings serially arranged along said anchor frame;
    a support frame comprising upstanding post members connected to and supporting said base member of said anchor frame;
    leg means, an adjustment means for adjustably connecting said leg means to said post members, and means for adjustably connecting said leg means to an operating table; said adjustment means operable to clamp said post members and thus said anchor frame at a preselected height;
    at least one resilient band adapted for connection of a retractor thereto; and,
    means for connecting said at least one resilient band to one of said anchor rings.

2. Apparatus in accordance with claim 1 including adjustable clamping means connecting said extension member to said base member.

3. Apparatus in accordance with claim 1 including a second extension member connected to said base member and spaced from said first extension member.

4. Apparatus in accordance with claim 3 including adjustable clamping means connecting said second extension member to said base member, said adjustable clamping means including means for permitting arcuate movement of said extension about the axis of said base member.

5. Apparatus in accordance with claim 1 including means for grasping said resilient bands to anchor said bands to said anchor rings.

6. Apparatus in accordance with claim 5 wherein said means comprises hemostats.

7. A surgical instrument for anchoring retractors for separating an incision and maintaining said incision in a predetermined open position, said instrument comprising:
    a retractor anchor frame comprising a first rigid member having a plurality of spaced apart, projecting, serially arranged anchor rings thereon;

a pair of extension members having spaced apart projecting anchor rings serially arranged therealong;

first and second adjustable clamping means connecting respectively said extension members in spaced apart relation to said first rigid member so as to project substantially perpendicular thereto; said clamping means including means for permitting rotation of said extension about said first rigid member and for clamping said extension in a predetermined position about said member;

a support frame for said anchor frame, said support frame comprising at least one vertically oriented post connected to said first rigid member of said anchor frame, and a horizontally extending leg member adapted for connection to an operating table; and, means adjustably coupling said post to said leg and for adjusting the position of said retractor anchor frame.

8. A surgical instrument in accordance with claim 7 including a plurality of resilient bands having retractors connected thereto and at one end thereof; and means for connecting said resilient bands to selected ones of said anchor rings.

9. A surgical instrument in accordance with claim 8 wherein said retractors are S-shaped.

10. A surgical instrument in accordance with claim 8 wherein said means for connecting said band to said rings comprises hemostats.

* * * * *